(12) United States Patent
Risk et al.

(10) Patent No.: US 8,712,692 B2
(45) Date of Patent: Apr. 29, 2014

(54) METHOD OF MEASURING THE FLUX OF A SOIL GAS

(75) Inventors: David A. Risk, Heatherton (CA); Hugo J. Beltrami, Pomquet (CA); Nicholas R. Nickerson, Kentville (CA); Gordon McArthur, Kentville (CA)

(73) Assignee: St. Francis Xavier University, Antigonish (CA)

( * ) Notice: Subject to any disclaimer, the term of this patent is extended or adjusted under 35 U.S.C. 154(b) by 413 days.

(21) Appl. No.: 13/139,489

(22) PCT Filed: Dec. 15, 2008

(86) PCT No.: PCT/CA2008/002186
§ 371 (c)(1),
(2), (4) Date: Sep. 29, 2011

(87) PCT Pub. No.: WO2010/069030
PCT Pub. Date: Jun. 24, 2010

(65) Prior Publication Data
US 2012/0035850 A1     Feb. 9, 2012

(51) Int. Cl.
*G06F 19/00*     (2011.01)
*G01V 9/00*     (2006.01)
*G01N 1/22*     (2006.01)

(52) U.S. Cl.
CPC ............ *G01N 1/2205* (2013.01); *G01N 1/2294* (2013.01)
USPC ............. 702/2; 702/24; 73/23.32; 73/114.72; 73/864.83; 73/863.23

(58) Field of Classification Search
CPC ....................... G01N 1/2294; G01N 2013/003; G01N 27/4074; G01N 27/407; G01N 21/3504; G01N 33/004; G01N 7/14; G01N 1/22; G01N 33/24; G01N 2001/2285; G01N 2001/4016; G01V 9/007; F01N 11/00; F01N 11/007

USPC ............. 702/2, 24; 73/23.32, 114.72, 864.83, 73/864.74, 863.23, 864.81, 864.51; 204/401, 431; 422/82.01; 701/114; 340/632

See application file for complete search history.

(56) References Cited

U.S. PATENT DOCUMENTS

| 4,938,194 A * | 7/1990 | Kato et al. ................... 123/688 |
| 6,598,458 B1 * | 7/2003 | Edwards et al. ............... 73/19.1 |

(Continued)

FOREIGN PATENT DOCUMENTS

| CA | 2507354 A1 | 11/2006 |
| CA | 2547413 A1 | 11/2006 |

(Continued)

OTHER PUBLICATIONS

International Search Report of PCT/CA2008/002186, Jul. 28, 2009, Stephen Hartling.

*Primary Examiner* — Carol S Tsai
(74) *Attorney, Agent, or Firm* — Bereskin & Parr LLP

(57) ABSTRACT

A method for determining a flux of a gas contained in a medium through a boundary of the medium comprises 1) measuring at least twice with a probe a concentration C of the gas over a time interval $\Delta t$ and 2) determining the flux of the gas using the following mathematical equation: (I) where F is the gas flux, D is the diffusivity value and $\Delta C$ is a variation in the gas concentration during the time interval $\Delta t$. The probe is placed proximate the boundary. The probe has a gas inlet, a cavity, a gas concentration sensor and a membrane. Each element is in fluid communication with each other so that the gas flows from the gas inlet through the membrane and contacts the gas concentration sensor.

$$F = \left(D\frac{\partial C(z,t)}{\partial z}\right)_{z=0} = \frac{\sqrt{D}\,\Delta C}{\sqrt{\pi \Delta t}} \quad (I)$$

23 Claims, 4 Drawing Sheets

(56) References Cited

U.S. PATENT DOCUMENTS

| | | | |
|---|---|---|---|
| 7,266,459 B2 * | 9/2007 | Kimoto et al. | 702/24 |
| 7,520,186 B2 * | 4/2009 | Risk | 73/864.74 |
| 7,596,993 B2 * | 10/2009 | Fukagai et al. | 73/114.72 |
| 7,779,669 B2 * | 8/2010 | Fukagai et al. | 73/23.32 |
| 7,856,899 B2 * | 12/2010 | Furtaw et al. | 73/864.73 |
| 2005/0288847 A1 * | 12/2005 | Inoue et al. | 701/114 |
| 2007/0266800 A1 * | 11/2007 | Risk | 73/863.23 |
| 2007/0273540 A1 * | 11/2007 | Inoue et al. | 340/632 |
| 2008/0060939 A1 * | 3/2008 | Inoue et al. | 204/401 |
| 2008/0060941 A1 * | 3/2008 | Ieda et al. | 204/431 |
| 2008/0196489 A1 * | 8/2008 | Fukagai et al. | 73/114.72 |
| 2008/0196490 A1 * | 8/2008 | Fukagai et al. | 73/114.72 |
| 2008/0196702 A1 * | 8/2008 | Fukagai et al. | 123/688 |
| 2009/0084172 A1 * | 4/2009 | Fukagai et al. | 73/114.72 |
| 2009/0301234 A1 * | 12/2009 | Risk | 73/864.83 |

FOREIGN PATENT DOCUMENTS

| | | |
|---|---|---|
| WO | 2007124585 A1 | 11/2007 |
| WO | 2008070922 A1 | 6/2008 |

* cited by examiner

METHOD OF MEASURING THE FLUX OF A SOIL GAS

FIELD OF THE INVENTION

The present invention relates generally to the field of soil gas measurement. More specifically, the invention relates to a method of measuring the flux of a soil gas.

BACKGROUND OF THE INVENTION

Measurement and monitoring of gas fluxes is a common practice in many areas of the Earth. For example, in volcanically active regions, the measurement and monitoring of gas fluxes can be an indicator of changes in volcanic activity and could even be critical in saving human lives in the event that $CO_2$ gases are built up in the soil and have the potential for catastrophic release. In the oil industry, measurements of volatile hydrocarbon emissions can be a non-intrusive and inexpensive way of finding potential hydrocarbon deposits. At contaminated sites, flux measurements can either be used to map out the extent and severity of the contamination or can be implemented to determine natural attenuation rates. Moreover, flux measurements are also used extensively in the budgeting of greenhouse gases, both to determine the rate of natural emission of greenhouse gases from soil and groundwater sources as well as to evaluate flux from aquatic systems.

Most commonly, soil gas fluxes are measured using either Fick's law of diffusion (also known as the concentration gradient method), by the static chamber method, or by eddy covariance. All of these methods, however, have some shortcomings.

The concentration gradient method requires the measurement of two or more concentrations at different depths in the soil profile and often involves disturbing the soil to install monitoring equipment. This affects both the soil structure and the gas transport regime. This method, however, typically underestimates fluxes because of improperly constrained diffusion coefficients or effective soil gas diffusivity values. Concentration profiles of natural or injected $^{222}$Radon or other tracers have been used to determine diffusivity in the field, but many researchers defer to empirically-derived approximations that require soil-specific input parameters, such as the Millington model or other recent improved models. Unfortunately, diffusivity models tend to perform better in some soils than in others. Alternatively, there are several approaches that allow for laboratory testing of intact soil cores collected in the field. These have the advantage that soil gas diffusivity can be determined on a relatively small spatial and temporal scales that would otherwise be difficult to measure with either $^{222}$Radon concentration profiles, or in highly organic substrates, such as soil litter, which are not clearly dealt with in diffusivity model approximations. There remains, however, the potential for changes to soil physical properties (e.g. soil aggregation, compaction etc) that could have a large influence on resulting values.

Aside from diffusivity, other limitations of the gradient approach include the intensiveness of sampling as several simultaneous concentration measurements are required for one flux calculation, frequent gas well installation challenges, the high degree of lateral variability in gas concentrations owing to subsurface heterogeneity, the need for post-processing of data, and the added error resulting from the multiple necessary steps of gas extraction, sample transport, and laboratory analysis.

The static chamber method measures soil gas flux using an accumulator that, in its simplest form, consists of an inverted can placed on the soil surface. Upon deployment, high concentrations of soil gases drive flux out from the soil by diffusion and into the lower concentration headspace of the chamber. Mass accumulation of gas into the chamber over time is used to calculate fluxes. In the past, simple manual chamber techniques have used one or more samples of the chamber headspace over an accumulation period, usually several minutes or more. Gas analysis is typically conducted in the laboratory by gas chromatography. A linear, exponential, or polynomial model is used to fit the data and to calculate fluxes. Many design improvements have been added to sampling chambers over the 60-year history of the technique. Over the last 15 years, good automated chamber instruments have become available for survey $CO_2$ measurement that allow computer control of the technique and gas analysis within the instrument, delivering instant real-time data to the user. Users typically use these instruments as survey tools to sample emissions at various points across the landscape. Permanent chambers are also available with an open top, but with an arm that seals the chamber at a predetermined time interval. Similar to automated survey chambers, these incorporate a detector and microprocessor that can deliver real time data.

Despite the advantages of chamber techniques (simplicity, commercial availability, real-time data), they have several important limitations. Chambers are not suitable for use during winter where snow is present, particularly the permanent deployment types with moving external parts. Commercially available systems are expensive and have been found to underestimate fluxes in certain cases and overestimate them in others. The use of static chambers also requires that a collar be installed on the ground surface, which may temporarily increase gas fluxes and also, if left in the soil for long periods, may aid in the development of a microenvironment that is not indicative of the flux conditions that would be seen elsewhere in the sampling site. There also exist design problems with static chambers in that the estimated flux can be affected by changes in atmospheric pressure as well as by buildup of fluxing gas in the chambers, causing fluxes to slow with time. Other drawbacks include the inability to estimate fluxes from large portions of the soil surface and, in the case of the static chamber methods, the need to return and manually sample the gases built up in the chambers. This latter problem makes a time intensive process that has the possibility for contamination and error. Chambers also provide a non-continuous estimate of gas fluxes since the chamber needs to be manually removed from the soil surface and replaced to initiate a new measurement.

Eddy covariance (also known as micrometeorological technique, eddy correlation or eddy flux) is a method used to estimate gas fluxes over large areas. The basis of this method is the measurement of gas transport vectors from a tower, particularly the vertical turbulent fluxes within atmospheric boundary layers. Simultaneous measurement of vertical transport and concentrations at two or more heights above the ground surface are required to execute the method. This is a technique reserved for highly skilled specialists because it is mathematically complex, requires care in setting up stations, and requires significant data conditioning and post-processing. To date, there is neither a uniform terminology nor a single methodology for the eddy covariance technique.

While the technique can return data on average gas fluxes from a large area (up to several square kilometers), the key assumptions that underlie the method expose obvious limitations. Firstly, fluxes must be fully turbulent, and most of the net vertical transfer must be done by eddies, which means that data cannot be acquired under windless conditions in which eddies are not present, such as frequently occurs at night. The measurement footprint of the station changes constantly according to both wind speed and direction. This means that areas outside the area of interest might be frequently unintentionally monitored. In addition, terrain must be flat and uniform and atmospheric density fluctuations must be negligible. Moreover, eddy covariance stations are extremely expensive to buy, deploy, and run, yet they still suffer from large temporal gaps in collected data. Recent research has shown that the footprint is also a considerable drawback for industrial purposes, such as carbon capture and storage, because eddy covariance stations are not capable of resolving large magnitude emissions from limited areas.

Hence, all of these known methods for measuring the flux of a soil gas still have something left to be desired. There is therefore a clear need for a method of measuring the flux of a soil gases that overcomes the shortcomings of known methods.

SUMMARY OF THE INVENTION

It is an object of the present invention to provide a method of measuring the flux of a soil gas that overcomes or mitigates one or more disadvantages of known methods, or at least provides a useful alternative.

The method of the present invention provides the advantages of being easy to put in practice, requiring only a few pieces of equipment that are easy to deploy, and requiring little human intervention.

In accordance with one embodiment of the present invention, there is provided a method for determining a flux of a gas contained in a medium through a boundary of the medium. The method comprises 1) measuring at least twice with a probe a concentration C of the gas over a time interval $\Delta t$, and 2) determining the flux of the gas using the following mathematical relation:

$$F = \left( D \frac{\partial C(z, t)}{\partial z} \right)_{z=0}$$

where F is the gas flux, D is the diffusivity value of the gas and C(z,t) is the gas concentration as a function of both depth and time. The probe is placed proximate the boundary. The probe has a gas inlet, a cavity, a gas concentration sensor and a membrane. Each element is in fluid communication with each other so that the gas flows from the gas inlet through the membrane and contacts the gas concentration sensor. Optionally, the mathematical relation is the following mathematical equation:

$$F = \frac{\sqrt{D} \Delta C}{\sqrt{\pi \Delta t}}$$

where $\Delta C$ is a variation in the gas concentration during the time interval $\Delta t$.

Another option is that the method includes the step of determining the diffusivity value of the gas, either by imposing the diffusivity to the gas at a predetermined value with the membrane or by measuring the diffusivity of the gas through the boundary of the medium.

BRIEF DESCRIPTION OF DRAWINGS

These and other features of the present invention will become more apparent from the following description in which reference is made to the appended drawings wherein.

DETAILED DESCRIPTION OF THE INVENTION

Figure 1:
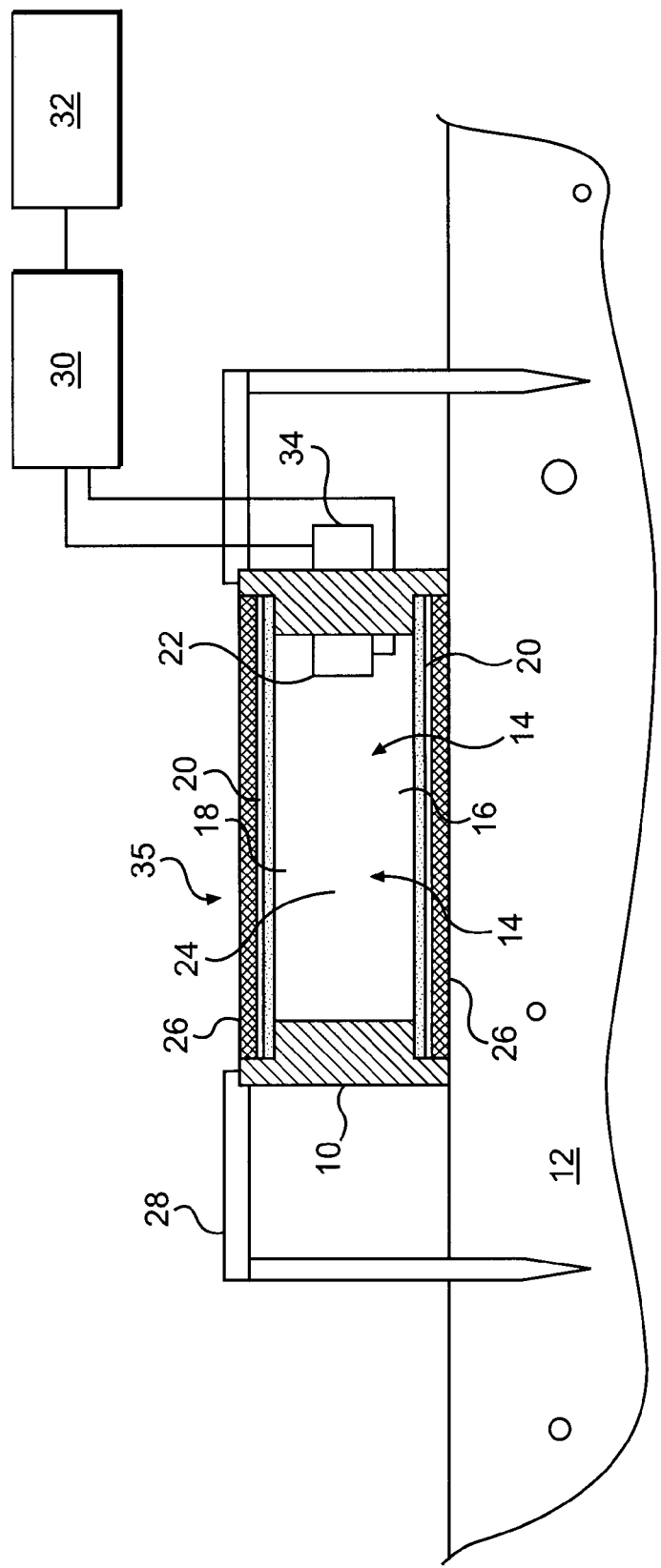
FIG. 1 shows a cross-sectional side view of a probe placed on a soil in which a soil gas is distributed, in accordance with an embodiment of the present invention.

The present invention relates to a land-based flux measurement technique. This measurement technique uses a mathematical approximation and requires only a single high-resolution concentration measurement and tightly constrained values of soil gas diffusivity. Like eddy covariance, the present technique is based on continuous transport and concentration measurements. However, it is appreciably simpler, due to more predictable and static nature of diffusive gas transport processes in shallow subsurface. Implementation of measurement equipment requires very little site disturbance, and offers a continuous, rather than occasional, estimate of gas flux. The measurement equipment is relatively inexpensive to deploy and run, is reliable, and in some configurations may also be used to monitor gas fluxes over larger spatial scales without sacrificing small-scale resolution. Although the present method may be generally used to determine the flux of a gaseous component originally distributed within a medium, it is particularly useful to determine the flux of a soil gas flowing out of a soil and will be described with respect to that application herein. For example, the present method of measuring gas flux may be used to monitor soil gas fluxes in carbon capture and storage sites, in ecological applications, in a variety of non-$CO_2$ embodiments, and in any application that requires uninterrupted measurements of soil gas flux from the soil surface whether in harsh, fair, or unattended deployments.

There have been several recent papers in which the change in heat flux to the ground surface during the past few centuries has been calculated using borehole temperature profiles. Similarly, a study in which sensible heat fluxes from the Earth's surface on shorter timescales (weeks and days) has also been conducted using the same methods. The particularity of this method of heat flux calculation lies in the fact that it requires only a single measurement of temperature to calculate heat flux. Prior to these publications, it was thought that the calculations required two or more temperature probes in the case of sensible heat fluxes, and was impossible in the case of paleoclimate reconstructions.

Heat is conducted through a medium, such as the ground, by the process of diffusion. Diffusion is the same physical process that governs the movement of gases from the soil or aquatic environment into the atmosphere. An aspect of the present invention lies in that it has been found that the equation used to determine gas fluxes is quite similar to that used for determining heat fluxes.

For a homogenous soil, the one-dimensional, time-dependant concentration of gas in the soil is formulated as:

$$\frac{\partial C(z,t)}{\partial t} = -D\frac{\partial^2 C(z,t)}{\partial z^2} \tag{1}$$

where C(z,t) is the gas concentration function, t is time, D is the diffusion coefficient and z is depth in the soil. This can be solved for an arbitrary concentration function, $C_0$ (t), to yield:

$$C(z) = \frac{z}{2\sqrt{D\pi}}\int_0^\infty C_0(t)t^{-3/2}\exp\left(\frac{-z^2}{4Dt}\right)dt \tag{2}$$

If each change of gas concentration in the soil is considered to be an instantaneous step change happening over the period of time Δt, this function can be integrated to yield the simplified expression:

$$C(z) = \Delta C \mathrm{erfc}\left(\frac{z}{2\sqrt{D\Delta t}}\right) \tag{3}$$

where ΔC is the step concentration change magnitude and erfc is the complimentary error function.

The instantaneous concentration gradient in the soil at any time is calculated as:

$$\frac{dC(z)}{dz} = \frac{-\Delta C}{\sqrt{\pi D \Delta t}}\exp\left(\frac{-z^2}{4D\Delta t}\right) \tag{4}$$

The vertical concentration flux is related to the concentration gradient by Fourier's equation in one dimension:

$$q(z,t) = -D\frac{\partial C(z,t)}{\partial z} \tag{5}$$

The substitution of 4 into 5 yields $$q(z,t) = \frac{D\Delta C}{\sqrt{\pi D\Delta t}}\exp\left(\frac{-z^2}{4D\Delta t}\right) \tag{6}$$

Because the instantaneous surface flux at the time of a step concentration change is infinite, the average flux over the time interval is obtained by integration:

$$q_{ave}(z=0) = \frac{1}{\Delta t}\int_{\Delta t} \frac{D\Delta C}{\sqrt{\pi D}}\frac{dt'}{\sqrt{\Delta t}} \tag{7}$$

which simplifies to:

$$q_{ave} = \frac{2\sqrt{D}\,\Delta C}{\sqrt{\pi \Delta t}} \tag{8}$$

This final equation allows the determination of the change in flux using concentrations from only one depth, or in the present case, at the soil-air interface.

The relevant conditions for the equation to be applicable are: 1) atmospheric concentrations of the gas in question must remain constant, if this condition is not true the equation can be modified; however, this condition is satisfied over short time spans in the case of most gases; 2) the initial condition of the equation is that gas flux is zero at time zero, meaning that all values derived from the equation are changes from the initial gas flux and; 3) equation (6) only applies where diffusion is the dominant means of transport and the diffusion coefficient can be measured accurately. Apparent diffusion coefficients can be used in the equation, but must be used with care as they have the possibility of severely under or over estimating diffusive flux.

When calculating the total flux from the soil surface, it is important to realize that equation (6) becomes iterative. The flux will consist of the initial flux plus all of the changes in flux or, expressed mathematically:

$$q(t) = q_0 + \sum_{t_i}^{t_f}\frac{\sqrt{D}\,\Delta C}{\sqrt{\pi \Delta t}} \tag{9}$$

where $q_0$ is the initial surface flux, and the summation is carried out in a time step fashion. For example, supposing an initial flux of 1 μmol/m²/s and a change in flux for the first 5 minutes of 0.1 μmol/m²/s, then the new flux at 5 minutes is 1.1 μmol/m²/s, if during the next 5 minutes a drop in flux of −0.2 μmol/m²/s occurs, then the new flux at 10 minutes will be 1+0.1−0.2=0.9 μmol/m²/s, and so on.

For soil gas concentration measurements taken at or near the air-soil interface, the change in flux from the original condition may then be expressed by:

$$F = \left(D\frac{\partial C(z,t)}{\partial z}\right)_{z=0} = \frac{\sqrt{D}\,\Delta C}{\sqrt{\pi \Delta t}} \tag{10}$$

where F is the flux, D is the media diffusivity and ΔC is the step change in concentration over the time step Δt (s). Equation (10) will now be referred to as the Flux Solution.

FIG. 1 depicts an embodiment of a typical deployment of a probe 10 at a soil-atmosphere interface, i.e. at the surface, of soil 12. Soil gas 14 is distributed in the soil 12. The probe 10 has a gas inlet 16 and a gas exhaust 18. At least one of the gas inlet 16 and the gas exhaust 18 is equipped with a membrane 20 of known diffusivity. The probe 10 is also equipped with a gas concentration sensor 22, located in a probe cavity 24 between the gas inlet 16 and the gas exhaust 18 so that the soil gas 14 entering the probe 10 is free to flow from the gas inlet 16 to the gas exhaust 18 through at least one membrane 20 installed at the gas exhaust 18. The membranes 20 may be covered by a stainless steel mesh 26 to prevent cuts to the membranes 20 when the probe 10 is inserted in the soil 12.

Advantageously, both the gas inlet 16 and the gas exhaust 18 may each be equipped with one membrane 20 to prevent water from infiltrating the probe 10. The membrane 20 may be a waterproof breathable spun polyolefin membrane, of the type made by DuPont™ under the trademark Tyvek™.

Preferably, the membranes 20 should approach the diffusivity of free air to mimic the lower atmospheric boundary layer. This way, the membranes 20 will not perturb subsurface concentration gradients and all soil gas emissions will pass through the probe 10 as if it were in free air. In some instances, it is desirable to have a probe cavity 24 of the probe 10 at a higher concentration than surrounding air. This increases the magnitude of concentration change in the probe 10 for a given flux change, thus maximizing resolution. In some other cases, for example if the soil 12 is very porous and diffusivity in the soil 12 is very high, it may not be possible to manufacture membranes whose diffusivity is lower than the that of the soil 12. When such a situation occurs, 2-D diffusive effects will be initiated in the soil 12 and some soil gas 14 will start flowing around the probe 10. These 2-D effects can be minimized or compensated for during later data processing.

The measurement surface area of the probe 10, i.e. the membrane 20 area in contact with the soil 12 surface, may be made large or small. However, small footprints will minimize the depth to which 3-D concentration gradient effects penetrate the soil 12 due to a continued presence of the probe 10 on the soil surface.

Advantageously, with the method of the present invention, diffusivity within the soil 12 does not really matter since the membranes 20 impose a given diffusivity by acting as a thin synthetic "soil" at the soil-atmosphere interface. Indeed, the probe 10, and more particularly its membranes 20, function as a lab-calibrated artificial medium. With the method of the present invention, when diffusivity may be measured or imposed, the only other parameter required is a time series of concentration measurements. Consequently, once the probe 10 is assembled, its diffusivity is measured in a laboratory.

Figure 2:
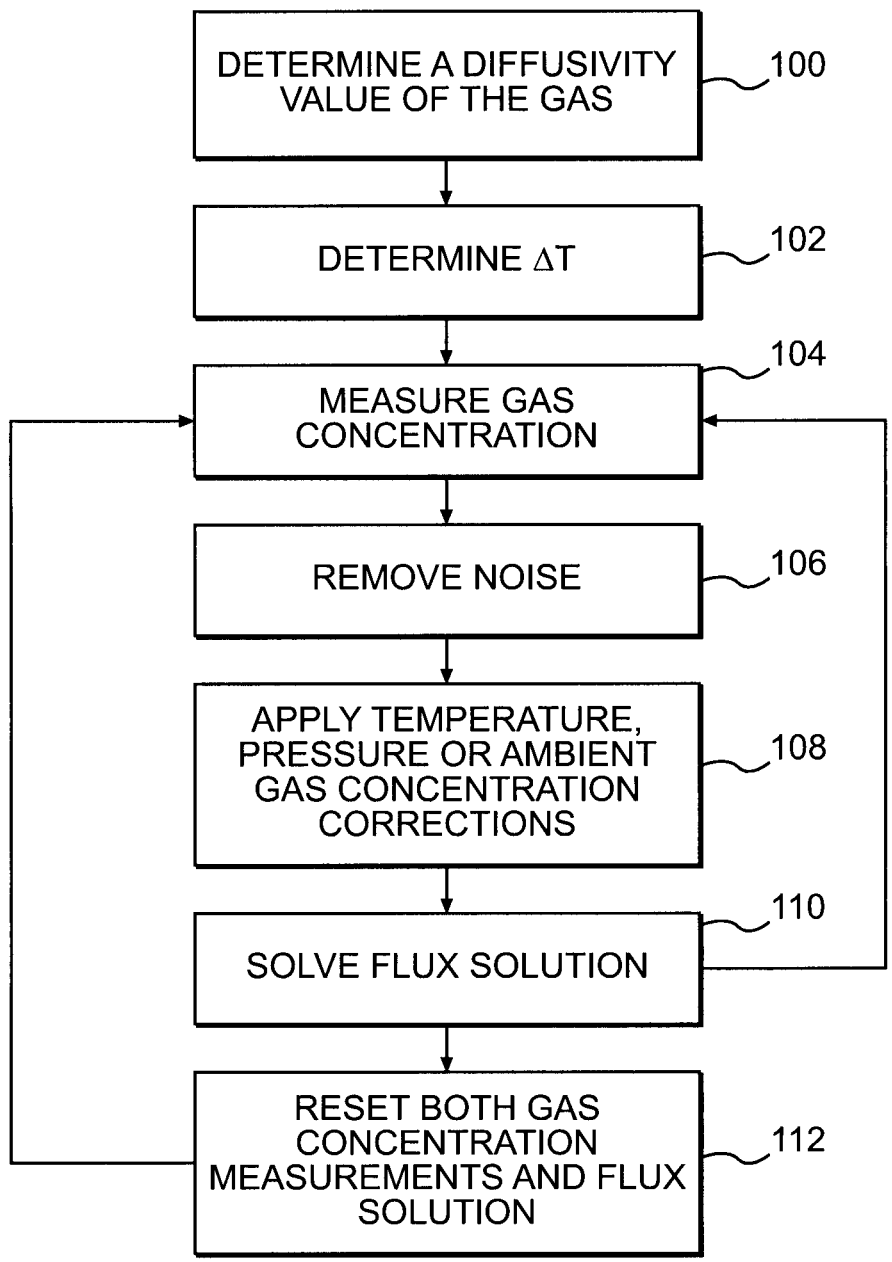
FIG. 2 is schematic view of a method of determining the flux of a gas in accordance with an embodiment of the present invention.

Reference is now concurrently made to FIG. 2. Before being able to solve the Flux Solution, the diffusivity value of the gas must be known. It is possible to determine the diffusivity value of the gas, identified at step 100, in different ways. For example, in the present example, the gas diffusivity is imposed by the membrane 20, if only one membrane is present, or membranes 20, if both are present. This diffusivity value may be experimentally determined beforehand, most likely with test equipment such as a Flux Generator testing device. Alternatively, the diffusivity of the gas could be determined experimentally with known methods, as will be described below. In use, the probe 10 is placed on the soil 12 in which the soil gas 14 is dissolved or distributed. It may be noted that although one single probe 10 may be deployed, as depicted in FIG. 1, more than one probe could be deployed to cover a larger area if desired.

Before proceeding with measurements, it is typical to determine a time interval $\Delta t$, as step 102, at which the gas concentration sensor 22 will take its measurements. Usually, the gas concentration sensor 22 takes its measurements at a time interval typically between 1 and 60 seconds. These measurements create a time series of soil gas concentration measurement data that is sent to the data acquisition system 30. The time interval must be set as a function of the lab-measured diffusivity of the membranes 20 of the probe 10 otherwise the Flux Solution will not calculate accurate flux rates. Indeed, the mathematical derivation of the Flux Solution artificially creates infinite flux as the time interval $\Delta t$ approaches zero. Because this is not realized in nature, the time interval $\Delta t$ must be selected so that these transient infinite fluxes are averaged out and the actual flux rate is realized, with the appropriate time interval $\Delta t$ being a function of the diffusivity of the membranes 20 of the probe 10.

By simulating time varying soil fluxes at several diffusivities, the following relationship was found:

$$\log(\Delta t) = -0.998276 \cdot \log(D) - 4.47512 \quad (11)$$

When applying the Flux Solution, it is recommended that these guidelines for $\Delta t$ be followed. Otherwise, the calculated flux could be significantly over or underestimated.

The probe is fixed into place by a fixation system 28, such as a collar that extends into the soil at some distance from the probe in order not to influence the measurements. The fixation system 28 may play a double duty: 1) stabilize the probe 10, and 2) force 1-D diffusion of the soil gas 14 near the probe 10.

Alternatively, the probe 10 may be deployed below the surface and still maintain the same functionality as when deployed at the surface. The primary advantage of deploying the probe 10 below the surface is that it sits below the active zone of the soil 12 where soil gases 14 are produced naturally. Consequently, the flux measurements are then limited to soil gases 14 coming from deeper in the subsurface. This is a technique to eliminate noise in a deep signal of interest that may be overprinted near the air-soil interface by additional biogenic sources of the same soil gas.

In the present example, the probe 10 is placed on the soil 12 such that its gas inlet 16 is positioned directly in contact with the soil 12 and the gas exhaust 18 is positioned at a distance over the soil, separated by the probe cavity 24. Once the probe 10 is properly installed on the soil 12, the soil gas 14 flows into the probe 10 through the gas inlet 16. As the soil gas 14 flows in the probe cavity 24 towards the gas exhaust 18, the soil gas 14 comes in contact with the gas concentration sensor 22 which measures a concentration of the soil gas 14 at step 104. The soil gas 14 continues flowing towards the gas exhaust 18, through its membrane 20 and eventually into the atmosphere. It may be noted that, as opposed to many known methods that require that the gas concentration be measured at a minimum of two locations, the method of the present invention requires only that the gas concentration be measured at a single location.

The gas concentration sensor 22 is connected to a data acquisition system 30, itself connected to a data processing unit 32. The data acquisition system 30 receives and records all soil gas concentration measurement data sent from the gas concentration sensor 22. The data may be sent either directly, via a cable 34 or via a wireless connection. For example, the gas concentration sensor 18 could be connected to a transmitter that remotely transmits to a receiver connected to the data acquisition system 30. Different known and future data transmission technology could be used, such as radio waves, cellular phone network, Internet, etc but will not be described in more details here as a person skilled in the art could easily adapt any convenient data transmission technology to the invention. Alternatively, the data acquisition system 30 and the data processing unit 32 could be incorporated into the probe 10 as a standalone device.

The data acquisition system 30 records data on electronic memory or on a storage media, such as a computer hard drive. Finally, the data processing unit 32, which may be a computer, solves the Flux Solution using the data received from the gas concentration sensor 22 and the pre-determined value of the gas diffusivity to determine the soil gas flux. The data processing unit 32 may solve the Flux Solution either after all data has been received, or alternatively may solve the Flux Solution simultaneously to the gas concentration sensor 22 taking measurements of the soil gas concentration.

In some situations it may be required to measure the concentration of soil gas outside the probe 10, that is the ambient atmospheric gas concentration at the probe level, (for example, where soil fluxes and variability is very low relative to any atmospheric variation). The necessity to measure the ambient atmospheric gas concentration arises from the fact that the mathematical equation assumes that the atmospheric gas concentration is constant, which is seldom the case. After processing of the mathematical equation, the measurements of the ambient atmospheric gas concentration may be used to correct the calculated results of soil gas flux. In order to gain the capability of measuring the ambient atmospheric gas concentration, an optional second gas concentration sensor 34 may be used on the outside of the probe 10. When multiple probes 10 have been deployed on the soil 12, only one shared second gas concentration sensor 34 may be sufficient for all probes 10 if spatial variability of atmospheric gas concentrations is low.

Optionally, to get more accurate results, some corrections to the soil gas concentration measurement data time series may be applied. The time series may be filtered for noise if required to, as shown in step 106. This may be accomplished by known methods such as frequency rejection or other simple techniques like moving averages. Furthermore, the time series of soil gas concentration measurement data may be corrected for atmospheric fluctuations that may have influenced the diffusivity of the soil gas, shown at step 108. Soil gas concentration measurements taken by the second soil gas concentration sensor, which have also been related to the data acquisition system 30, are used to calculate this correction. Finally, it may be required to correct the soil gas concentration measurement data for ambient pressure and temperature in case the soil gas concentration sensor does not already compensate for it.

Once the soil gas concentration measurement data time series has been corrected, it is ready to be computed by the processing unit 32. The processing unit 32 solves the Flux Solution at step 110. As stated before, the Flux Solution does not return an absolute flux magnitude, but rather a change in flux from the original condition. The value of the original soil gas flux may be measured different ways. It is possible to carefully observe the initial gas concentration measurement data upon deployment of the probe 10 as the soil gas rises to its equilibrium concentration inside the probe 10 from its original atmospheric concentration value. This data can be processed through the Flux Solution to deliver accurate initial flux values as long as the initial atmospheric concentration measurement is representative of the actual ambient atmospheric concentration. All subsequent values of flux calculated using the Flux Solution from this point onwards are departures from this initial condition. Alternatively, it is possible to use another technique, such as with a static chamber, at the time of deployment of the probe 10 such that the processing unit 32 may deliver the real flux magnitude through time as an output.

The Flux Solution does not necessarily have to be solved for the complete soil gas concentration measurement data time series. This flexibility proves to be useful when a disturbance has happened in the measured soil gas concentration data. Disturbance will usually result in a rapid and lasting step change in the measured soil gas concentration data. This is a good indicator that a condition has changed, such as an animal tripping on the probe 10, or a snowfall covering it. If a non-random error seems to have occurred in the data, it is possible to select only the portion of the data that seems intact. Such errors could be caused by a jarring of the probe that affected the way it coupled with the soil. By resetting the Flux Solution, it is potentially possible to recover the measurement data from the probe that has been partially kicked over or dislodged from the soil. By re-calibrating the diffusivity of the probe 10 and by restoring the initial conditions of the probe as it was before its disturbance, it is possible to recover soil gas concentration measurement data, or to continue monitoring, after almost any type of disturbance. Frequent resetting, especially of the initial calculated flux values, is likely beneficial to long term stability.

Resetting of the probe 10 is particularly useful in the case where snow accumulates both on the soil surface and on the probe 10, as shown at step 112. The presence of snow modifies the atmosphere around the probe 10. This new atmosphere may have a gas concentration different than the gas concentration in the free atmosphere. When this is the case, it is convenient to purge the probe cavity 24 with air from this new atmosphere taken from around the probe 10, either manually or by automated control. The air needed for this purging operation should come from a suitable reservoir at the soil surface that continually adjusts its concentration to match that of the new snowy atmosphere or free atmosphere via a waterproof gas permeable membrane. Since the purging is effectively like deploying the probe 10 anew, it is possible to carefully observe, as previously described, the initial gas concentration measurement data as the soil gas rises to its equilibrium concentration inside the probe 10. The initial flux value may then be established through solving the mathematical equation of the Flux Solution, which is used afterwards to measure deviations from this initial value.

This same resetting technique may be used for the probe 10 when deployed below the surface, to reset the concentration measurements and, consequently, the solution to the Flux Solution after rain, biogenic production, or another event that has altered the concentrations of gas above the probe 10. Deploying, re-deploying, or purging the probe 10 with air having ambient atmospheric gas concentration (most likely ambient air around the probe) all provide the same result: they allow the gas concentration inside the probe 10 to re-start equilibration from the ambient value. Resetting of the gas concentration inside the probe 10 and consequently of the Flux Solution allows the probe 10 to re-calibrate itself after a change in environmental condition: a new initial condition of gas concentration is established and gas concentration deviations are measured from that point on to calculate the flux values in time by the processing unit 32.

It may be possible to cause the processing unit 32 to reset the Flux Solution by imposing a constant concentration on an atmospheric side 35 of the probe 10. This may be achieved by pre-calibration of the probe 10 under constant concentration condition. This is possible because diffusion through the probe 10 will always result in a particular internal concentration at a given flux rate since diffusivity and $\Delta z$ are always fixed. This pre-calibration must be incorporated into the real-time Flux Solution calculations if they are done in an automated fashion by the processing unit 32. It is recommended that recalibration be done frequently.

It has been found that under some specific conditions, it may be preferable to measure the actual soil diffusivity using different known equipment. Such measurement of the soil diffusivity may be conducted by known methods. An example of such a technique is disclosed by Risk in published U.S. patent application Ser. No. 10/419,082. In this method, $CO_2$-free air is made on-site and introduced in the probe, temporarily interrupting the soil gas concentration measurements. This might have to be done once per day or once per week.

Figure 3:
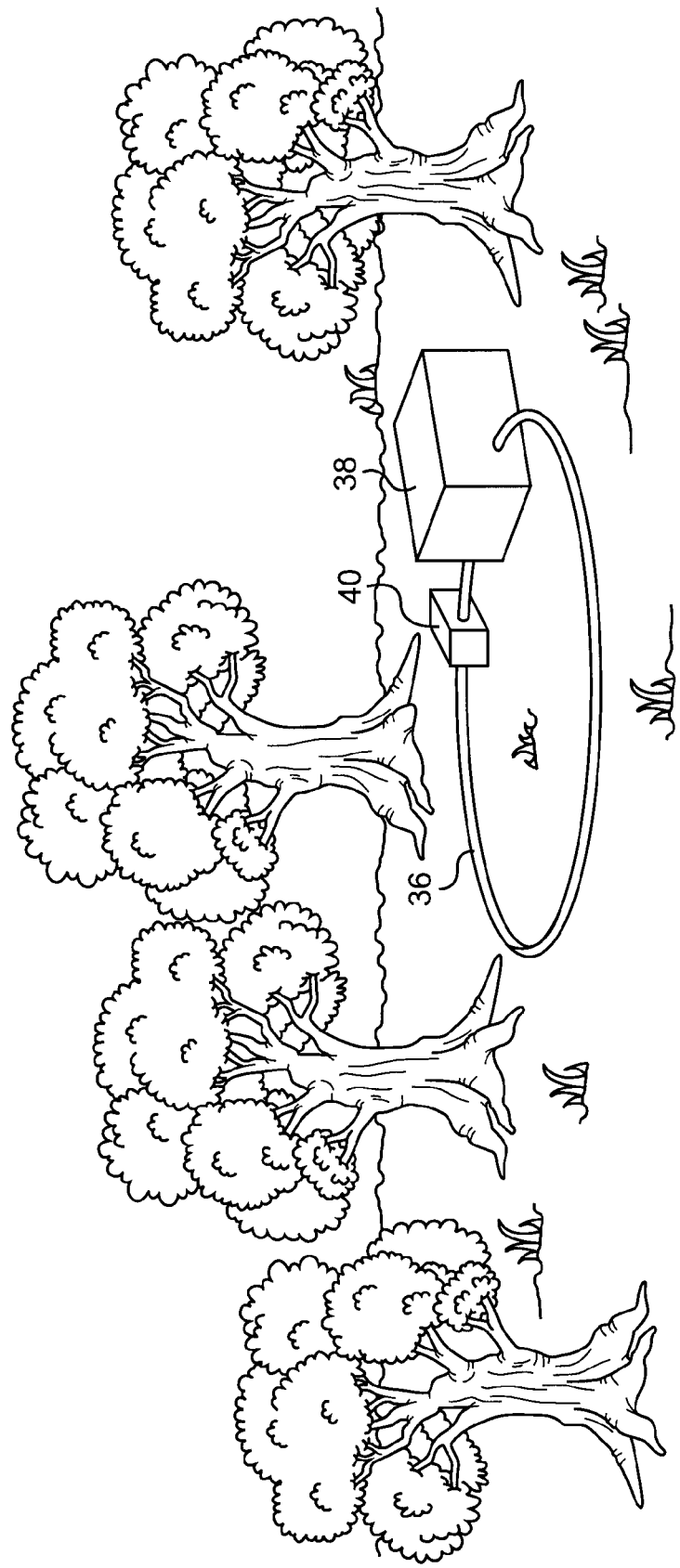
FIG. 3 is a perspective view of an apparatus used in the determination of the flux of the soil gas over a large spatial scale in accordance with another embodiment of the present invention.

A second embodiment of the present invention is now described. Reference is made to FIG. 3. In this embodiment, a known measurement technique is used to measure soil gas concentration data over a large spatial scale. This system of measurement uses a semi-permeable polyvinyl tube 36 connected to a recirculating pump 38 and a gas analyzer 40. The tube 36 allows unrestricted diffusion of the soil gas into its interior, where it is circulated in a closed loop, allowing the tube 36 to reach equilibrium with its surroundings quickly. After equilibrium has been reached, the soil gas may be drawn off the loop and sampled by the gas analyzer 40. Since the tube 36 is constantly in equilibrium with its surroundings, small spatial variation in soil gas concentrations are averaged by the circulating air inside the tube 36. This averaging gives a representative gas concentration for the entire area with which the tube 36 is in contact, rather than a point measurement. Soil gas diffusivity must be measured with a known technique, such as the one disclosed by Risk in published U.S. patent application Ser. No. 10/419,082.

Figure 4:
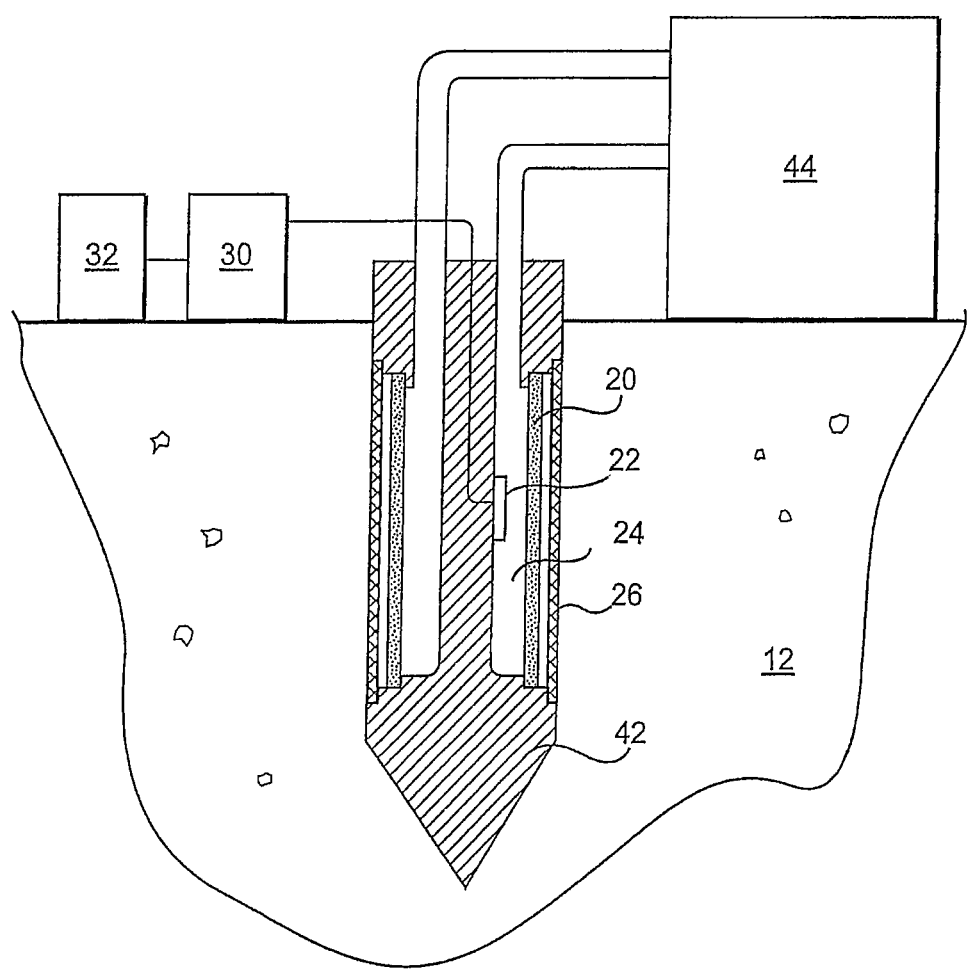
FIG. 4 shows a cross-sectional side view of another model of probe inserted in soil in which the soil gas is distributed, in accordance with another embodiment of the present invention.

A third embodiment is now described, with reference to FIG. 4. In the present embodiment, the single-point Flux Solution is coupled to a simultaneous measurement of soil gas diffusivity. Risk, in published U.S. patent application Ser. No. 10/419,082, describes an automated method and system for use in determining diffusivity values in-situ. However, rather than the described technique relying on a continuous flow membrane probe buried in the soil and coupled to an above ground control/measurement system, the probe 42 of the present embodiment is deployed at the soil-atmosphere interface to measure fluctuations in soil gas concentration, while still connected to a similar above ground control/measurement system 44. Diffusivity need be measured only infrequently, such as once per day, due to the slow changes in soil moisture that influences the diffusivity magnitude. This leaves significant periods where the probe 42, which is now a dual-purpose probe capable of both measuring soil gas diffusivity and soil gas concentration, could continuously track soil gas concentrations at the soil-atmosphere interface. The soil gas concentration measurements are then used to solve the Flux Solution between diffusivity measurements.

The present invention has been described with regard to preferred embodiments. The description, as much as the drawings, were intended to help the understanding of the invention, rather than to limit its scope. It will be apparent to one skilled in the art that various modifications may be made to the invention without departing from the scope of the invention as described herein, and such modifications are intended to be covered by the present description. The invention is defined by the claims that follow.

I claim:

1. A method for determining a flux of a gas contained in a medium through a boundary, the method comprising:
    measuring at least twice with a probe a concentration C of the gas over a time interval $\Delta t$, said probe being placed proximate the boundary, said probe having a gas inlet, a cavity, a gas concentration sensor and a membrane in fluid communication with each other so that the gas flows from said gas inlet through said membrane and contacts said gas concentration sensor; and
    determining the flux of the gas using the following mathematical relation:

$$F = \left( D \frac{\partial C(z,t)}{\partial z} \right)_{z=0}$$

where F is the gas flux, D is a diffusivity value of the gas and C(z,t) is said gas concentration as a function of both depth and time.

2. The method of claim 1 wherein said mathematical relation is the following mathematical equation:

$$F = \frac{\sqrt{D}\,\Delta C}{\sqrt{\pi \Delta t}}$$

where $\Delta C$ is a variation in the gas concentration over the time interval $\Delta t$.

3. The method of claim 2 further comprising determining said diffusivity value of the gas.

4. The method of claim 3 further comprising determining said time interval $\Delta t$ as a function of said diffusivity value of the gas.

5. The method of claim 4 wherein said diffusivity determining comprises imposing said diffusivity to the gas at a predetermined value with said membrane.

6. The method of claim 5 wherein said probe further comprises a gas exhaust in fluid communication with said gas inlet, said cavity and said gas concentration sensor.

7. The method of claim 6 wherein said gas exhaust is equipped with a second membrane, said determining comprises imposing said diffusivity to the gas at a predetermined value with said membranes.

8. The method of claim 4 wherein said determining of said diffusivity value of the gas comprises measuring a diffusivity of the gas through the boundary of the medium.

9. The method of any one of claims 1 to 8, wherein said measuring occurs at a single location.

10. The method of claim 2 further comprising correcting said gas concentration measurement based on at least one of a temperature, a pressure, or an ambient atmospheric concentration of the gas outside of said probe.

11. The method of claim 2 further comprising conditioning said gas concentration measurement to remove undesired noise.

12. The method of claim 2 wherein said solving occurs simultaneously with said measuring.

13. The method of claim 2 further comprising resetting said concentration measuring of the gas.

14. The method of claim 13 wherein said resetting further comprises moving said probe away from said boundary and sequentially placing said probe back proximate said boundary so as to significantly influence said gas concentration measurement.

15. The method of claim 13 wherein said resetting further comprises purging said probe with a second gas substantially different from the measured gas so as to influence said gas concentration measurement.

16. The method of claim 13 wherein said resetting further comprises purging said probe with an ambient air surrounding said probe so as to influence said gas concentration measurement.

17. The method of claim 2 further comprising measuring an initial flux of the gas through the boundary of the medium.

18. The method of claim 2 wherein the medium is soil.

19. The method of claim 2 wherein the medium is water.

20. The method of claim 2 further comprising storing said data in an electronic memory.

21. The method of claim 2 further comprising sending said data over Internet.

22. The method of claim 1 wherein the boundary is a boundary of the medium.

23. The method of claim 1 wherein the boundary is a boundary of said probe.

* * * * *

UNITED STATES PATENT AND TRADEMARK OFFICE
CERTIFICATE OF CORRECTION

PATENT NO.        : 8,712,692 B2                     Page 1 of 1
APPLICATION NO.   : 13/139489
DATED             : April 29, 2014
INVENTOR(S)       : David A. Risk et al.

It is certified that error appears in the above-identified patent and that said Letters Patent is hereby corrected as shown below:

Claims

Column 11, line 56, claim 1, delete "(z, t)" and replace with --(z,t)--.

Signed and Sealed this
Thirteenth Day of October, 2015

Michelle K. Lee
*Director of the United States Patent and Trademark Office*